United States Patent [19]

Kleesattel

[11] 4,277,174

[45] Jul. 7, 1981

[54] METHOD AND APPARATUS FOR THE MEASUREMENT OF HARDNESS TESTING INDENTATIONS

[76] Inventor: Claus Kleesattel, Apartado 4969, San Jose, Costa Rica

[21] Appl. No.: 110,779

[22] Filed: Jan. 9, 1980

[51] Int. Cl.³ .................... G01B 11/00; G01B 11/08
[52] U.S. Cl. .................................. 356/372; 356/378; 356/387
[58] Field of Search .............. 356/372, 378, 376, 387, 356/380; 73/81, 85; 250/560

[56] References Cited

U.S. PATENT DOCUMENTS

| | | | |
|---|---|---|---|
| 2,216,943 | 10/1940 | Hanemann | 73/85 |
| 3,754,436 | 8/1973 | Saxton | 73/81 |
| 3,822,946 | 7/1974 | Rynkowske | 73/81 |

FOREIGN PATENT DOCUMENTS 199203  8/1958  Fed. Rep. of Germany ........... 356/378

OTHER PUBLICATIONS

Rainiger, S., "Eine Anordnung zur Photometrischen Messung von Vickers-Härteeindrücken", Messtechnik, 12-1973, pp. 379–384.

Primary Examiner—Vincent P. McGraw
Assistant Examiner—Wm. H. Punter
Attorney, Agent, or Firm—Parmelee, Johnson, Bollinger & Bramblett

[57] ABSTRACT

A method and apparatus are provided for measuring the magnitude of spherical hardness testing indentations in solid surfaces by scanning the indentations with a light beam. Scanning is achieved by tilting the beam in one or several planes perpendicular to the testpiece surface through a point which is the center of rotation for the beam tilting as well as the center of curvature of the indentation area in the plane of tilting. At least the part of the indenter making contact with the indented surface is spherically shaped, and the scanning light spot follows an arcuate path in the indentation being measured. The scanning light beam is sent through a transparent indenter, or scanning is carried out directly on the indentation after removal of the indenter. The intensity of the light reflected from the indentation in the direction of incidence is continuously measured, and the angle between the two principle intensity variations on each scan serves for determining the magnitude of the indentation and thus the Brinell hardness of the tested surface.

14 Claims, 8 Drawing Figures

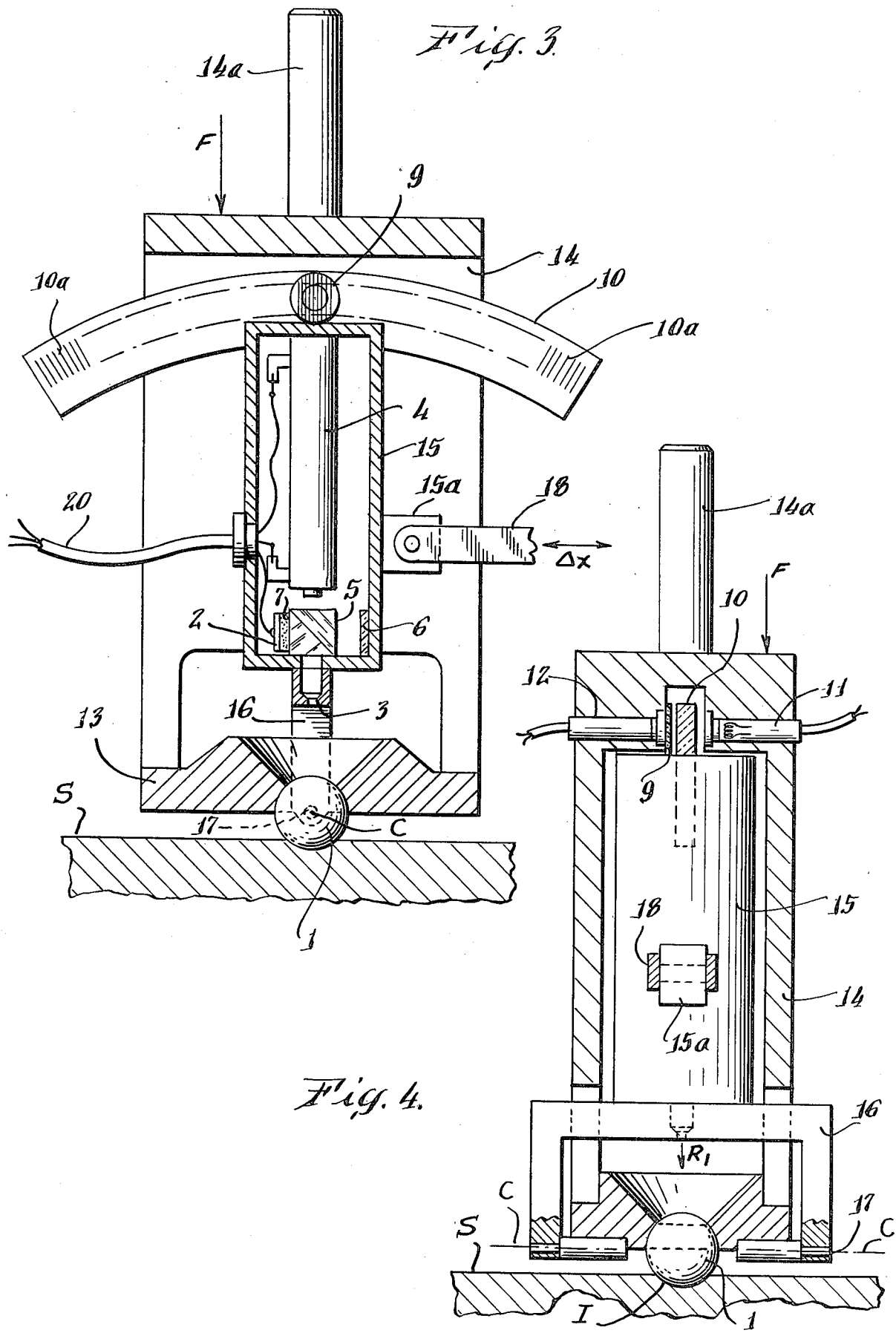

METHOD AND APPARATUS FOR THE MEASUREMENT OF HARDNESS TESTING INDENTATIONS

BACKGROUND OF THE INVENTION

This invention relates to methods and apparatus for measuring the magnitude of spherical indentations made for testing the hardness of the surfaces of solid material, and more particularly to such methods and apparatus which scan and measure spherical indentations with a light beam, the light beam being tilted in one or more planes through the center of the curvature of the indentation as well as perpendicular to the axis of tilting as it is scanned across the indentation being measured.

In my co-pending application Ser. No. 004,325, a method for measuring hardness indentations made in solid surfaces is disclosed in which a concentrated light beam is directed against the testpiece surface in a vertical direction. The light beam is translated parallel to the testpiece surface in at least one direction such that the light spot completely transverses the indentation at least once. During the crossing of the indent, the intensity of the light reflected from the indentation is measured within a predetermined angular range. The light intensity variation occurring when an edge of the indent is crossed, serves as an indicator for marking the initial and the final edge points of the scanned indentation which correspond to the distance between the two edge points of the indentation.

In an especially simple embodiment of the aforesaid application, a light spot is provided which moves along a straight line running through the center of the indent. Then the length of the distance travelled between two intensity variations occurring on the edges of an indent can be measured directly by means of a mechanical or electronic micrometer.

The aforesaid method has certain drawbacks when it is applied to measuring spherical indentations.

An especially designed generally ring-shaped photodetector is required in the aforesaid method. The light-sensitive area of a photodetector which is suitable for the Brinell test becomes relatively large owing to the big angular range of the reflected light, extending from approximately 30° to 80° measured against the vertical. If the measurement is attempted through a spherical indenter, the optical design for the above-mentioned angular range becomes complex. Also, the light that is reflected from the center region of the spherical indentation does not reach the photodetector. In a video display of an X-Y scan of a spherical indentation, the center region would appear as a dark spot of circular shape. Special electronic logic is required to account for the lack of signal when the scanning beam passes through the center region of the indent. Also, the scanning displacements $\Delta x$ corresponding to the distances between two edge points are rather small, and so are the corresponding rotation angles $\Delta\phi$ of the beam deflecting glass plate or prism. Then too, in most applications where a laser beam is used, a beam expander has to be incorporated in the system in order to get the necessary small spot diameter.

SUMMARY OF THE INVENTION

Accordingly, it is an object of this invention to provide a new and novel method and apparatus for performing the Brinell hardness test using spherical indentations which is not subject to the aforesaid drawbacks.

A further object of this invention is to provide a new and improved method and apparatus for performing hardness testing which employ commercially available photodetectors having small light sensitive areas.

Another object of this invention is to provide a new and novel method and apparatus for performing the Brinell hardness test of simple optical design which does not require a beam expander.

A still further object of the present invention is to provide a new and novel method and apparatus for measuring the magnitude of hardness testing indentations which use large scanning displacements (angles) thereby making it possible to use a simple means from determining the distance between two edge points of an indentation.

A still further object of this invention is to provide a new and novel method and apparatus for measuring the magnitude of hardness testing indentations which is particularly suited for indentations of essentially a circular shape.

In carrying out this invention in one illustrative embodiment thereof, a light beam is passed through the center of curvature of an at least partially spherical indenter which is being applied under load to a testpiece surface. The indent is scanned through the indenter by tilting the light beam about an axis parallel to the testpiece surface and in a plane coinciding with the indenter's center of curvature; such scanning to be done in at least one plane perpendicular to the testpiece surface. The light reflected from the indent in the direction of incidence is measured and the scanning angle between two intensity variations is measured for determining the size of the indentation.

Advantageously, because of the sharply defined indentation contour in accordance with the present invention, the measurement is made through the indenter under load on the testpiece. In principle, such measurement can also be carried out after having removed the indenter. In either case, only reflections from the indent are measured, the curves are very smooth and there is no "dark spot" in the output signal generated by the photodetector. Furthermore, conventional photodetectors may be employed. Additionally, a polar scan of the entire indentation can be implemented which is particularly useful in measuring indentations of essentially circular shape.

BRIEF DESCRIPTION OF THE DRAWINGS

The invention, together with further aspects, objects and advantages thereof, may best be understood by reference to the following description taken in connection with the accompanying drawings.

FIGS. 3 and 4 are two vertical sectional views of one embodiment of a device for measuring hardness indentations.

DESCRIPTION OF THE PREFERRED EMBODIMENTS

Figure 1:
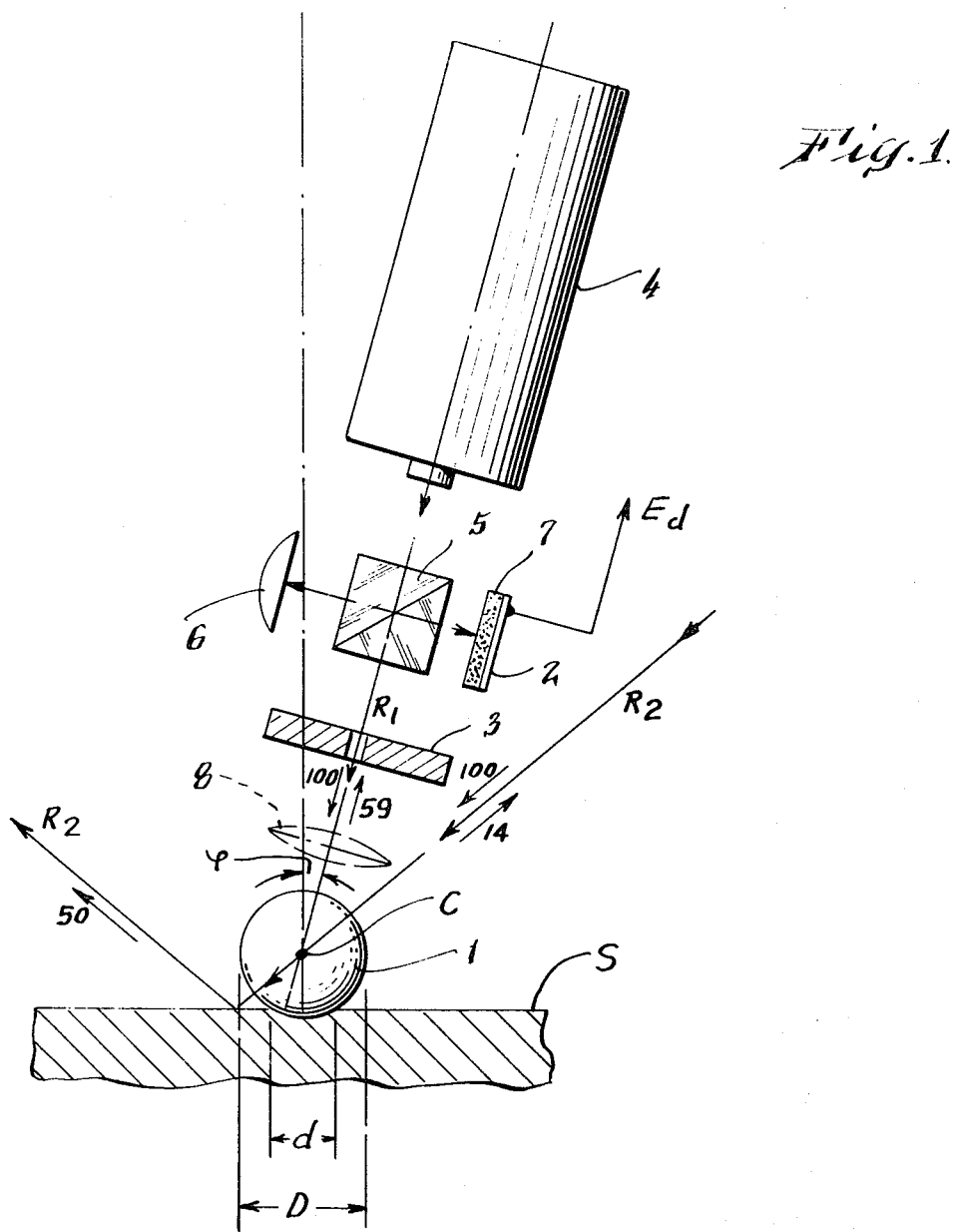
FIG. 1 is a schematic diagram of one embodiment of an apparatus for determining the size of a hardness indentation in accordance with one aspect of the present invention.
Figure 2:
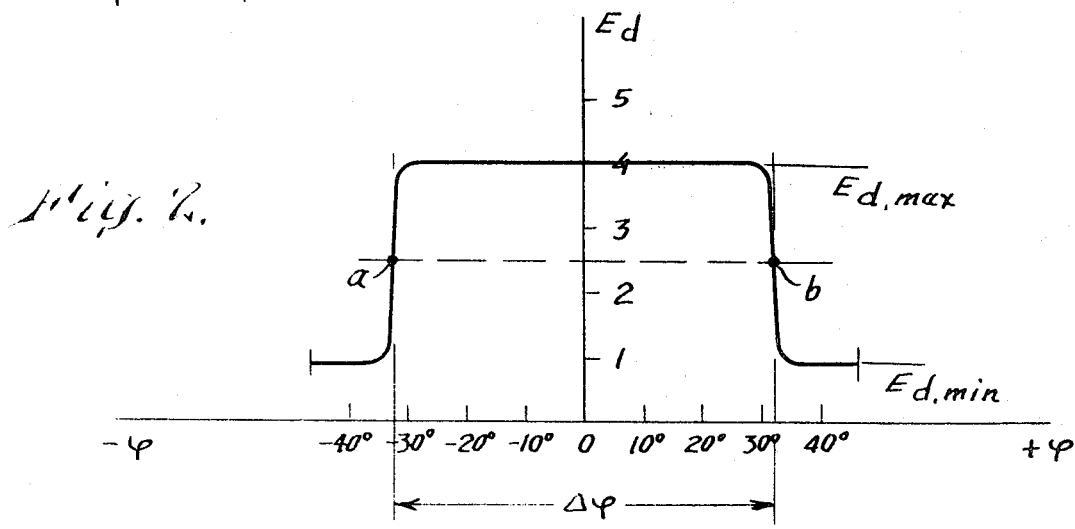
FIG. 2 is a graph of output voltage versus scanning angle of the incident light beam.

Referring now to FIGS. 1 and 2, a ball indenter 1, suitably mounted (not shown in FIG. 1), is forced with a given testing load against the surface S of the testpiece, where it produces an approximately spherical indent having a diameter d, which remains constant once the penetration process has come to a halt. Although the indenter 1 is shown as a complete sphere or ball it is only required to be spherical where it contacts the testpieces and accordingly may have different configurations, e.g. half spherical, half cylindrical, etc. The indenter is made from a hard, transparent material, e.g. sapphire. The ball diameter and the testing load are selected in accordance with the application, as outlined in the ASTM standards for hardness testing. The principle optical components shown in FIG. 1 are a light source 4, a beam-splitting cube 5, a stop 3, and a light-sensitive cell 2, e.g. a photodetector, with a diffusing plate 7 and a light-absorber 6. An optical component lens 8 may be provided which makes the light beam convergent so that the focal point falls exactly upon the indenter/indentation interface. The focal length of a sphere for parallel light is $f = nR/2(n-1)$ where R = ball radius, n = refractive index and f is measured from the center of the sphere. For a 10 mm Brinell ball made of sapphire, f equals 5.79 mm, i.e. the focal point lies behind the sphere. Using a helium-neon laser beam of 0.85 mm diameter, the spot diameter right at the surface of the ball measured 55 μm. Adding the lens 8, the diameter became 7 μm. However, no substantial increase in the slope of the curve shown in FIG. 2 was found. Therefore, one may make these measurements without the lens 8.

The output voltage of the photodetector is conveniently made proportional to the light intensity (watts per unit area). Measurements on Brinell indents through a sapphire ball produced smooth curves, just as shown in the example of FIG. 2. Also the resolving power was excellent. With $E_{d,max} = 1.05$ V and $E_{d,min} = 0.25$ V, a slope $dE_d/d\phi = 1.2$ V/grad was obtained. This refers to an indent of 4.73 mm diameter, and a tilting angle $\Delta\phi = 56.5°$, corresponding to a Brinell hardness of 161 (3000 kgf). Assuming summing up trigger errors of 20 percent on each edge of the indentation, the resulting error in the above-given hardness number would amount to 0.25 percent. Thus, the high resolving power of the measuring system combined with the distinct indentation contour (as seen through the indenter) produce an accuracy which is not matched by conventional Brinell testing equipment.

The entire optical system can be tilted about an axis C, which lies parallel to the surface S and which coincides with the center point of the ball 1. The incident light beam R1 passes through the beam-splitting cube 5 where part of it is reflected toward the light-absorber 6. After having passed the stop 3, it reaches the ball 1 with a relative intensity of '100'. Assuming that the testpiece is made of steel and the ball of sapphire, and that the wave length be equal to 600 nanometers, the light leaving the ball after reflection at the ball/testpiece interface combined with the light reflected at the upper ball face will amount to a relative intensity of '59', approximately. This reflected light follows practically the same path as the incident light beam, i.e. after passage through the stop 3 it is returned to the beam-splitter cube 5 and from there it goes to the photodetector 2, where it generates a corresponding voltage $E_d$.

Now, for a larger tilting angle $\phi$ of the optical system another incident light beam R2 is plotted which, after having passed through the ball 1, falls upon the undisturbed (original) testpiece surface, from where it is reflected with a relative intensity of '50', if the steel surface is polished to mirror finish. This reflected light does not reach the photodetector 2. Due to partial reflection at the two boundaries of the ball, the relative intensity of the light coming back to the beam-splitter cube is equal to '14' approximately. Thus, a light contrast of 59:14, or approximately 4:1, is obtained. The stop or slot 3 effectively prevents all such light from reaching the photodetector 2 which re-enters the ball 1 after reflection on the plane surface S of the testpiece.

In FIG. 2, the voltage $E_d$ produced by the photodetector 2 is shown as a function of the tilting angle $\phi$. The flanks of the curve, corresponding to an angular difference $\Delta\phi$, are a measure of the indentation diameter d defined by the following formula:

$$d = D \sin(\Delta\phi/2) \quad (1)$$

where D is the diameter of the ball indenter. Then one obtains for the Brinell hardness through substitution of the formula (1) for the diameter d:

$$HB = \frac{2F}{\pi D^2 [1 - \sqrt{1 - (d/D)^2}]} = \frac{2F}{\pi D^2 (1 - \cos\frac{\Delta\phi}{2})} \quad (2)$$

The symbol F means the testing load being applied.

Through well-known kinematic means it is possible to convert the angular motion into a rectilinear one being proportional to the diameter d of the indent, so that in formula (2) $\Delta x/mD$ would be substituted for $d/D$, where m is a transformation factor.

Owing to the upper limit for the penetration depth of ball indenters, as specified for all Brinell tests, it is possible to limit the tilting range to ±40 degrees. Hence, the maximum of $\Delta\phi$ will amount to 80 degrees.

For the purpose of deflecting the light that is reflected in the direction of the incident beam toward the photodetector 2, a beam-splitting cube 5 is applied, as shown in FIG. 1. For the same purpose other known devices like plates or membranes with metal coatings may be used.

Besides the stop 3 shown in FIG. 1, which eliminates light re-entering the ball 1 after reflection on the surface S, further stops may be placed elsewhere in the system, e.g. between the cube 5 and the photodetector 2. The well-known Porro prism, when placed between the beam-splitter and the photodetector, makes it possible to set narrow limits for the angles under which light can reach the photodetector 2.

Elliptical indentations occur frequently when Brinell tests are performed on anisotropic materials. For a correct measurement of Brinell indents having such shape one will carry out the tilting motion in two planes being perpendicular to each other and coinciding with the major and minor axis of the elliptic indent. Then, two different values $\Delta\phi$ are obtained whose arithmetic mean value is taken for calculating the hardness from formula 2.

FIGS. 3 and 4 show a device of simple construction for carrying out the hardness tests outlined above. The transparent ball indenter 1 is mounted in a metal socket 13 to which the applied testing load F is transmitted via a housing 14. The housing 14 has a cylindrical stud 14a where it is firmly attached to the loading mechanism (not shown) of the hardness testing machine. The testing load is taken by the upper portion of the housing 14 which is abutting the corresponding clamping means of the testing machine. During the loading and deloading cycles, the housing 14 is lowered and lifted together with all the other components of the measuring device.

The optical system is accommodated by the inner housing 15, which contains a laser 4, a beam-splitter 5, an absorber 6, and a photodetector 2 with a pertaining diffusor 4, i.e. it can be designed, for example, in the manner shown in FIG. 1. The stop 3 is shown in the form of a bore drilled into the yoke-shaped part 16. The inner housing 15 is attached to said yoke-shaped part 16, which is connected and supported by two pivotal pins 17 to the socket 13 for the ball indenter in such a way that it can be tilted as described before.

The positioning of the pivotal pins is such that the rotational axis C of the yoke 16 coincides with the center point of the ball indenter 1.

The tilting motion of the housing 15 is carried out by a servo-mechanism (not shown) which is linked to a protruding piece 15a by means of a push-rod 18. An electric cable 20 connects the light source 4 to a power supply, and the photodetector 2 to the electronic evaluation system.

Figure 5:
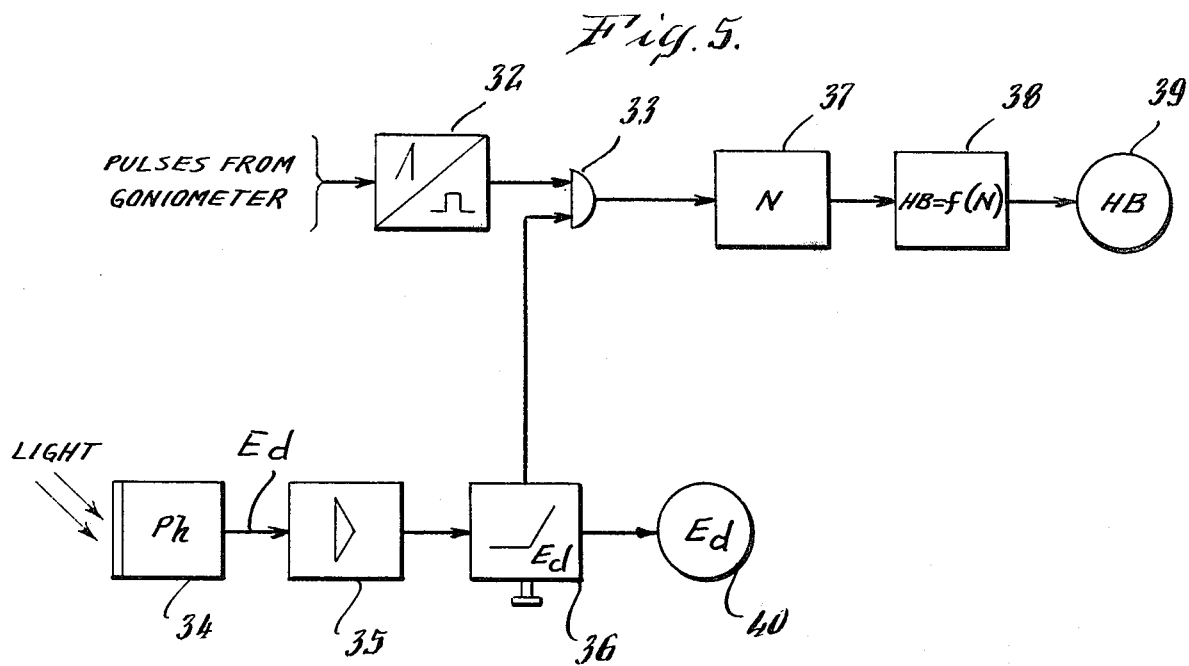
FIG. 5 is a schematic block diagram of an illustrative embodiment of an electrical circuit for measuring the hardness value of an indentation in accordance with this invention.

Now, referring to the measurement of the tilting angle $\Delta\phi$, an arched glass or plastic strip 10 bearing a line raster 10a drawn radially with respect to the rotational axis C is affixed to the upper end of the housing 15. A small raster-bearing plate 9 is mounted at the same height as strip 10 in the fixed housing 14 having a photodetector 12 positioned therebehind. Opposite to the photodetector 12 sits a stationary light source 11. When the housing 15 together with the raster-bearing strip 10 is tilted, a periodic variation of the light intensity, as perceived by the photodetector 12, takes place, whereby a sequence of voltage pulses are generated. The pulses are fed into an electronic evaluation system such as shown in FIG. 5 as will be described hereinafter. The angle measurement is made electronically with the tilting angle range $\Delta\phi$ being proportional to the number of counted pulses.

When the measurements on a number of indentations are carried out, the inner housing 15 is moved back and forth in the fashion of an inversed pendulum. Each indentation diameter measurement requires half of a pendulum oscillation. One complete measurement can be carried out in a fraction of a second which is added to the 'dwelling time' required for the hardness test. The latter amounts to 10 seconds for the standard Brinell test on steel. To those experienced in the art, it will be apparent that the tilting mechanics can be designed in many different ways. However, all such alternatives must have one common feature, namely, for a single scan the light beam is to be tilted in one plane and it must run through the ball center for all beam angles $\phi$ of the useful tilting range.

Referring to FIG. 5, which is an example of an electronic evaluation system, the pulses coming from the goniometer detector 12 are fed into a pulse-shaping circuit 32 to make them rectangular. The output of circuit 32 is fed into a gate circuit 33 whose output is fed into a pulse counter 37 which then is connected to a hardness indicating device 39 via an evaluation unit 38, e.g. an electronic calculator. The gate circuit 33 is controlled by a trigger circuit 36 which receives via amplifier 35 an amplified voltage $E_d$ as produced by the photodetector 34, receiving the light which is reflected in the direction of incidence as described in connection with FIG. 1. The shape of the voltage curve for one complete scan was presented in FIG. 2.

The trigger threshold is conveniently set to a value proportional to the median intensity of the reflected light $\overline{E_d} = \frac{1}{2}(E_{d,max} + E_{d,min})$ if this voltage is proportional to the intensity of the received light. The proper threshold setting can also be accomplished automatically through the incorporation of further electronic means. The dotted line in FIG. 2 corresponds to that mean voltage $E_d$. By suitable display means, the function $E_d(\phi)$ together with the trigger line can be made visible by a display unit 40.

The calculating or evaluating unit 38 is designed to produce the Brinell hardness number HB directly as a function of the number N of counted pulses.

Figure 6A:
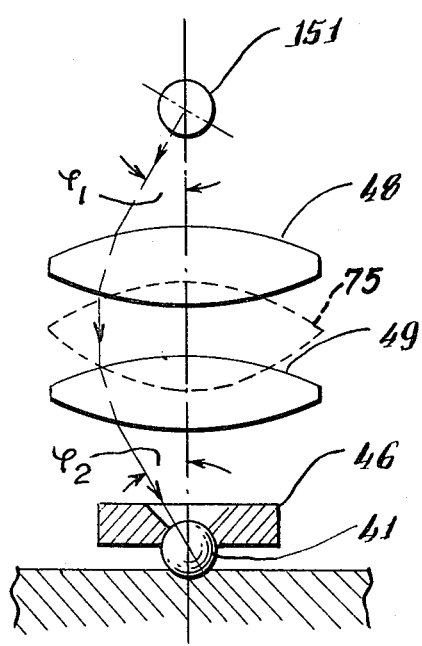
FIGS. 6a and 6b show elevational diagrammatic side views, partly in section, illustrating another embodiment of this invention.
Figure 6B:
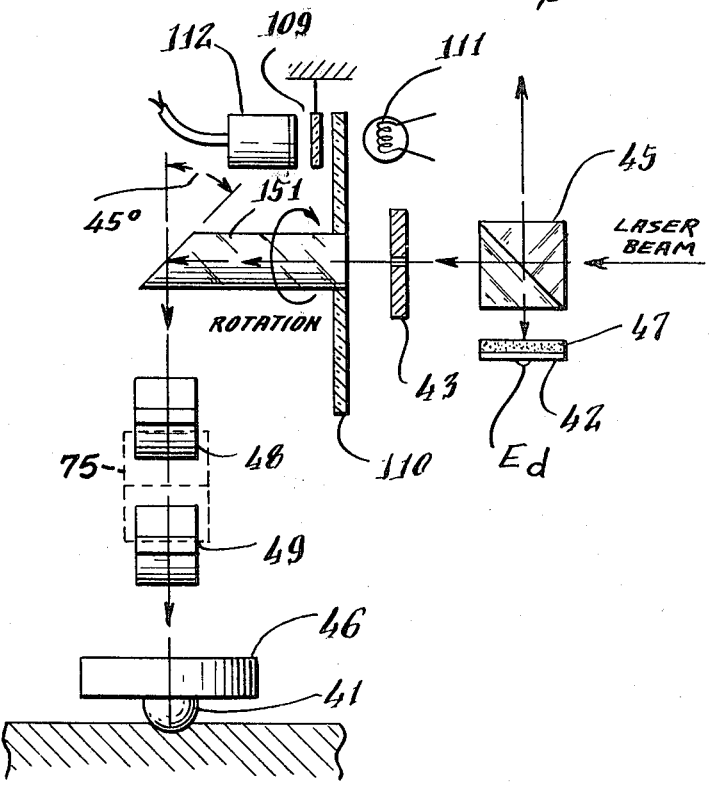

A second embodiment is schematically shown in FIGS. 6a and 6b. There the angular beam deflection is accomplished by optical means in the form of a rotating prism 151 in conjunction with one lens 75 (illustrated in phantom), but because of the required large aperture, preferably with two lenses 48, 49. The components 41, 42, 43, 45, 46 and 47 are similar to the ones shown in FIG. 1. Also the goniometer components 109, 110, 111 and 112 are similar to those shown in FIGS. 3 and 4.

The laser beam is deflected by an angle $\phi_1$ by means of a rotating rod or prism 151 with a reflecting endface to which a transparent disk 110, bearing a radial raster pattern, is attached. This rotating disk in conjunction with the fixed raster plate 109, light source 111, and a photodetector 112 provides a number of electronic pulses being proportional to the rotation angle $\phi$ of rod or prism 151. The light beam, reflected at the reflecting plane face inclined by 45 degrees, passes first through a collimating lens 48 and then through a concentrating lens 49. Since the beam deflection is to take place in one plane only, these lenses may be cylindrical form, or may be shaped as acylindrical lenses for the sake of correction of optical aberrations. The beam leaves the concentrating lens 49 towards the ball indenter 41 with an angle $\phi_2$, as shown. After passing through the ball 41 it is reflected at the indenter/indent interface. The reflected portion of the light is detected by the photodetector 42 and converted into a corresponding voltage which controls the electronic goniometer.

A condition for the proper functioning of the device is that the light beam pass through the center of the ball indenter 41 for all useful angles $15° \leq \phi_2 \leq 40°$. Furthermore, the angle $\phi_2$ must be a known and one-valued function of the angle $\phi_1$; preferably $\phi_2 = k\phi_1$, where k is a constant factor. The best and at the same time simplest condition is the one of symmetry, i.e. $\phi_2 = \phi_1$, as shown in FIG. 6a.

Figure 7:
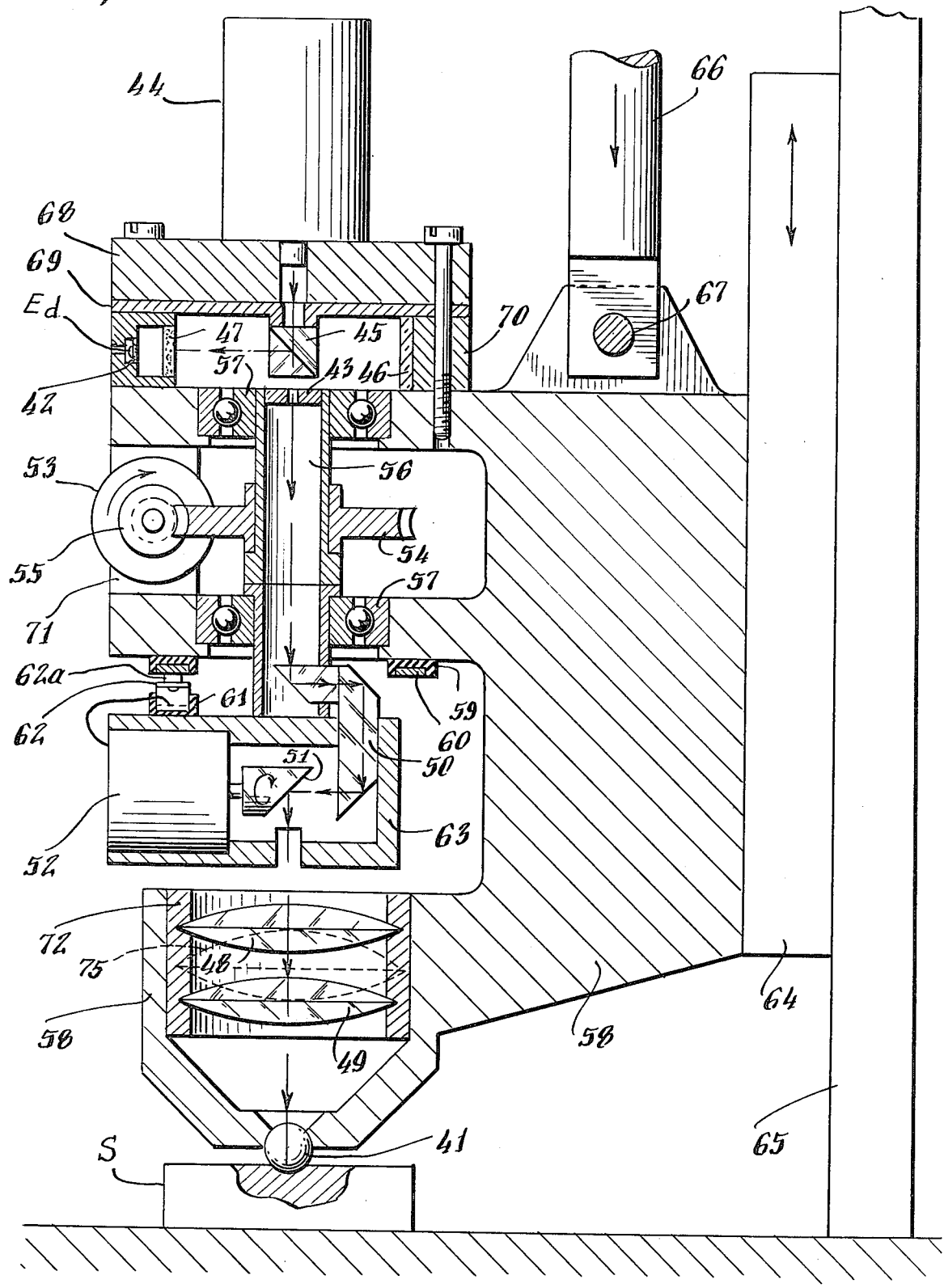
FIG. 7 is a detailed illustration, partly in cross-section, of the embodiment of FIGS. 6a and 6b.

In FIG. 7, an embodiment of this invention is shown incorporating the just outlined scanning system. In addition to this, mechanical means are shown which allow a complete area scan of the indentation, by performing a so-called polar scan. The angular deflection system, comprising a motor 52, an inclined plane mirror 51, and a housing 63, is attached to a rotatable tube 56 mounted in a pair of ball bearings 57 and made to spin at low speed by means of a worm gear 54, 55 energized by a second motor 53. A beam re-routing prism set 50 turns the light beam, coming from the laser 44 and being coaxial with the axis of tube 56, by 90 degrees in such a way that it hits a point on the rotating mirror plane 51 which is intersected by the rotation axis of motor 52. The speed of mirror 51 is made much bigger than the speed of tube 56 so that (if seen in projection) n scans through the center of the indent are made per revolution of housing 63, producing a polar scanning pattern.

The lenses 48, 49 are in a fixed position and therefore have to be spherical or, for the sake of correcting optical aberrations, aspherical.

Referring now to the other components, the light evaluation system comprises a beam-splitting cube 45, an absorber 46, a diffusor 47 and a photodetector 42. These components are housed and mounted in parts numbered 68, 69 and 70. The motor 53 of the worm gear is attached to the main housing 58 by means of a retaining bracket 71. Motor 52 is supplied with electricity via a slip ring 60 on which a contact 62a can slide. The latter is attached to a leaf spring 62 held by an insulator 61. The slip ring 60 is partially embedded in an insulating ring 59. The main housing 58 is attached to the movable portion of said slide assembly 64, 65. The portion 65 of the slide assembly is attached to the machine frame. The loading force F is exerted via a pressure bar 66 fastened to the main housing 58 by means of a bolt 67.

Now, with this type of testing device one finds for the Brinell hardness:

$$HB = \frac{2F}{\pi D^2 \left\{ 1 - \cos\left[-\frac{1}{2n} \sum_{l}^{n} (\Delta\phi)\right] \right\}} \quad (3)$$

where n is the number of radial scans through the center of the indent per revolution of the tube 56, to which housing 63 is attached. By suitable means of synchronization for the two motors 52, 53 the quantity 'n' is made constant.

The system as shown in FIG. 7 does not contain a goniometer. If the mirror 51 rotates with a constant and known speed, then it is possible to determine each $\Delta\phi$ through a time measurement, i.e. by measuring the ellapsed time between point 'a' (start of the count) and point 'b' (end of the count) on the curve shown in FIG. 2. Then, the summation sign in formula (3) will represent the sum of all ellapsed times from the 1st to the nth scan.

Summarizing the method of measuring spherical indentations in accordance with the present invention, the light beam penetrating the ball is reflected at the boundary between the indenter and the surface to be tested which is identical with the surface of the indent. At the ball/air interface, the light beam leaves the ball and reaches the original testpiece surface from where it is reflected in a different direction. Thus, the reflection is limited to the arc defined by the ball/testpiece interface. The tilting range for the reflection extends to both sides of the vertical up to those angles where the light spot hits the edges or periphery of the indentation. As a consequence, the light reflected in the direction of incidence varies its intensity twice if the tilting angle is made large enough. If the testpiece consists of metal, normally providing some degree of specular reflection in the region of contact, a good light contrast is achieved for the two situations, amounting to 4:1 on a steel specimen, or to 6:1 on an aluminum specimen, if the indenting ball consists of sapphire. A very smooth light curve (FIG. 2) is obtained because (a) of the usually mirror-like surface finish of the indentation area and (b) no light from the original testpiece surface which can be rough and wavy reaches the photodetector.

Since the indentation diameters of Brinell indents are relatively large, the light spot diameter need not be extremely small. Generally, a sharply focused white light beam will suffice. The transparent ball itself acts as a focusing lens. The convergence of the incident light beam can be adjusted in such a way that the smallest beam diameter (the focal point) coincides with the lower ball surface which is making contact with the testpiece.

For generating an extremely small light spot, one may use ultraviolet laser light. The use of such shortwave light, however, may cause some loss of contrast. On the other hand, to obtain the highest possible contrast, a light of longer wave-length, e.g. infrared laser light will be employed. Infrared light is also advantageous for all those testing conditions, where the surface of the indenter is easily attacked by the testpiece material, i.e. scratched, pitted, etc.

It will be apparent that for measuring the intensity of the reflected light any suitable type of photodetectors can be employed, e.g. photoconductors, photoelectric cells, photovoltaic cells, and others.

Since other modifications and changes varied to fit particular operating requirements and environments will be apparent to those skilled in the art, the invention is not considered limited to the examples chosen for purposes of illustration and covers all changes in modifications which do not constitute departures from the true spirit and scope of this invention.

What is claimed is:

1. The method of measuring the magnitude of spherical hardness testing indentations in testpiece surfaces utilizing a beam from a radiation source which is passed through a transparent indenter of at least partially spherical shape, the beam at the point of incidence being small with respect to the size of the indentation comprising the steps of:
   passing said beam through the center of curvature of an at least partially spherical indenter,
   tilting said beam about an axis parallel to the testpiece surface and coinciding with the center of curvature in the scanning plane, said tilting motion effected in at least one plane perpendicular to said testpiece surface,
   measuring the intensity of the radiation reflected from the indentation in the direction of incidence, and
   measuring the scanning angle between two intensity variations for determining the size of the indentation.

2. The method set forth in claim 1 in which the scanning and measurement steps are performed after the at least partially spherical indenter has been removed from the indentation being measured.

3. The method set forth in claim 1 or 2 in which said tilting motion includes simultaneously angularly rotating the plane of tilting to effect a polar scan of the indentation.

4. Apparatus for measuring the magnitude of hardness testing indentations in testpiece surfaces utilizing a beam from a radiation source which at the point of incidence is small with respect to the size of the indentation being measured comprising:

an indenter having a body which is spherical in at least the indenting portion thereof and transparent to said radiation source, scanning means for tilting said beam in at least one plane perpendicular to the testpiece surface and about an axis parallel to the testpiece surfaces and coinciding with the center of curvature of said indentation in said scanning plane, means for measuring the intensity of reflected radiation within a predetermined range defined by the scanning angle across said indenter, and means for measuring the scanning angle between two intensity variations which is a measure of the size of the indentation.

5. The apparatus set forth in claim 4 in which said indenter is a ball of hard material which is transparent for the wave length of the radiation source utilized and means for mounting said ball for applying an external force thereto.

6. The apparatus set forth in claim 5 wherein said means for mounting said ball comprises a socket for said ball to which said external force is applied.

7. The apparatus set forth in claim 4 having a housing, said radiation source, said means for measuring the intensity of reflected light and said means for measuring the scanning angle all mounted on said housing, and means for tilting said housing about an axis parallel to said testpiece surface which coincides with the center of curvature of said indenter.

8. The apparatus set forth in claim 4 wherein said means for measuring the intensity of reflected light comprises a photodetector, and stop means positioned in the path of said photodetector for preventing light from reaching said photodetector which has re-entered said indenter after reflections from an undisturbed area of said testpiece surface.

9. The apparatus set forth in claim 4 or 8 having an optical means for converging said radiation beam so that the smallest beam diameter coincides with the interface between said indenter and said testpiece surface.

10. The apparatus set forth in claim 4 wherein said scanning means includes means for turning said scanning plane through predetermined angles for producing a polar scan of the indentation.

11. Apparatus for measuring the magnitude of hardness testing indentations in testpiece surfaces and for effecting a polar scan of the indentation utilizing a beam from a radiation source which is small with respect to the size of the indentation being measured comprising:

an indenter having an at least partially spherical body which is transparent to said radiation beam, a rotary reflective surface for angularly deflecting said beam from said radiation source in a plane orthogonal to the testpiece surface and coinciding with the center of curvature of the indenting means, mechanical means for slowly rotating said rotary reflective surface about an axis normal to the testpiece surface and also coinciding with the center of curvature of said indenter, said beam passing through the center of curvature of said indenter, means for sensing the intensity of light reflected from said indentation as said indentation is being scanned by said beam, and means for measuring the size of the indentation using the intensity of the light reflected from said indentation.

12. The apparatus set forth in claim 11 having a collimating lens and a concentrating lens positioned between said rotary reflecting surface and said indenter.

13. The apparatus set forth in claim 11 or 12 in which the deflection angles measured at said rotary reflective surface and at said spherical indenter are equal.

14. The apparatus set forth in claim 11 having a single aspherical lens positioned between said rotary reflective surface and said indenter.

* * * * *